United States Patent [19]

Segato

[11] Patent Number: 5,139,513
[45] Date of Patent: Aug. 18, 1992

[54] APPARATUS AND METHOD FOR SUTURING

[75] Inventor: Giuseppe Segato, Arcugnano, Italy

[73] Assignee: Bieffe Medital S.A., Italy

[21] Appl. No.: 599,688

[22] Filed: Oct. 17, 1990

[30] Foreign Application Priority Data

Oct. 17, 1989 [CH] Switzerland .................. 3832/89

[51] Int. Cl.⁵ ........................................ A61B 17/115
[52] U.S. Cl. .................................. 606/219; 227/21; 227/179; 227/180
[58] Field of Search ............... 227/175, 176, 180, 19, 227/20, 21, 177, 178, 179, 181, 901; 606/219, 108, 153, 155

[56] References Cited

U.S. PATENT DOCUMENTS

| 4,289,133 | 9/1981 | Rothfuss | 227/19 X |
|---|---|---|---|
| 4,485,817 | 12/1984 | Swiggett | 227/179 |
| 4,573,468 | 3/1986 | Conta et al. | 227/179 |
| 4,606,343 | 8/1986 | Conta et al. | 227/178 |
| 4,667,673 | 5/1987 | Li | 606/153 |
| 4,671,445 | 6/1987 | Barker et al. | 227/19 |
| 4,817,847 | 4/1989 | Redtenbacher et al. | 227/19 |

Primary Examiner—Hien H. Phan
Assistant Examiner—Raymond D. Woods
Attorney, Agent, or Firm—Ostrolenk, Faber, Gerb & Soffen

[57] ABSTRACT

An apparatus for making surgical sutures in surgical operations, including a distal head part for making the sutures and receiving a cartridge containing staples and having a hollow punch, a control part at the other end and a flexible part transmitting to the distal head part control movements of the control part. The head part is detachable, and is not attached at the moment of insertion into the zone to be sutured. The head part is preferably replaced by a protective cap at the end of the flexible transmitting part. The protective cap allows easy insertion into an opening of a body part to be sutured. The cartridge is mounted to the head part in situ after the protective cap is removed and the head part is located in the zone in which the operation is to take place.

33 Claims, 6 Drawing Sheets

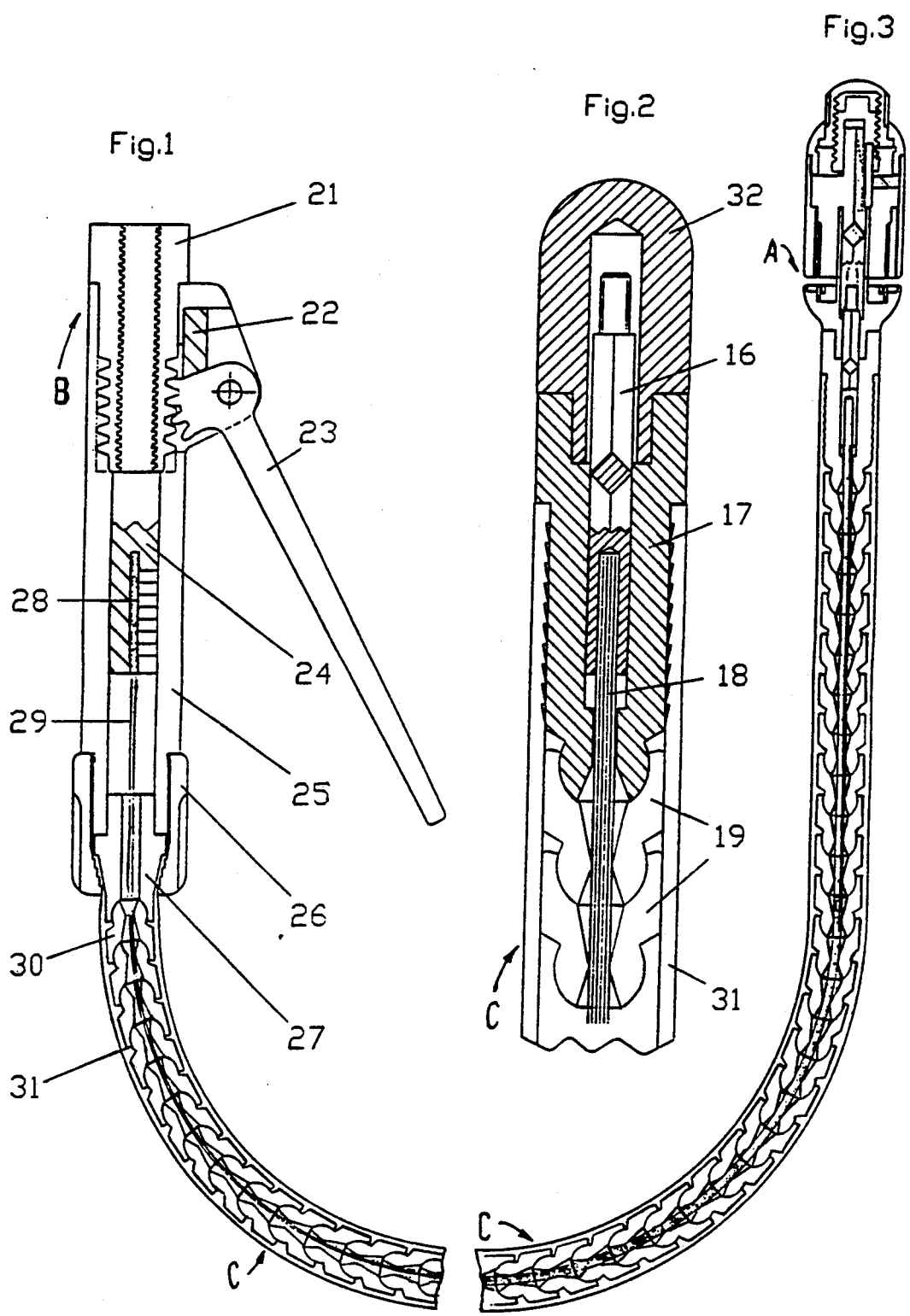

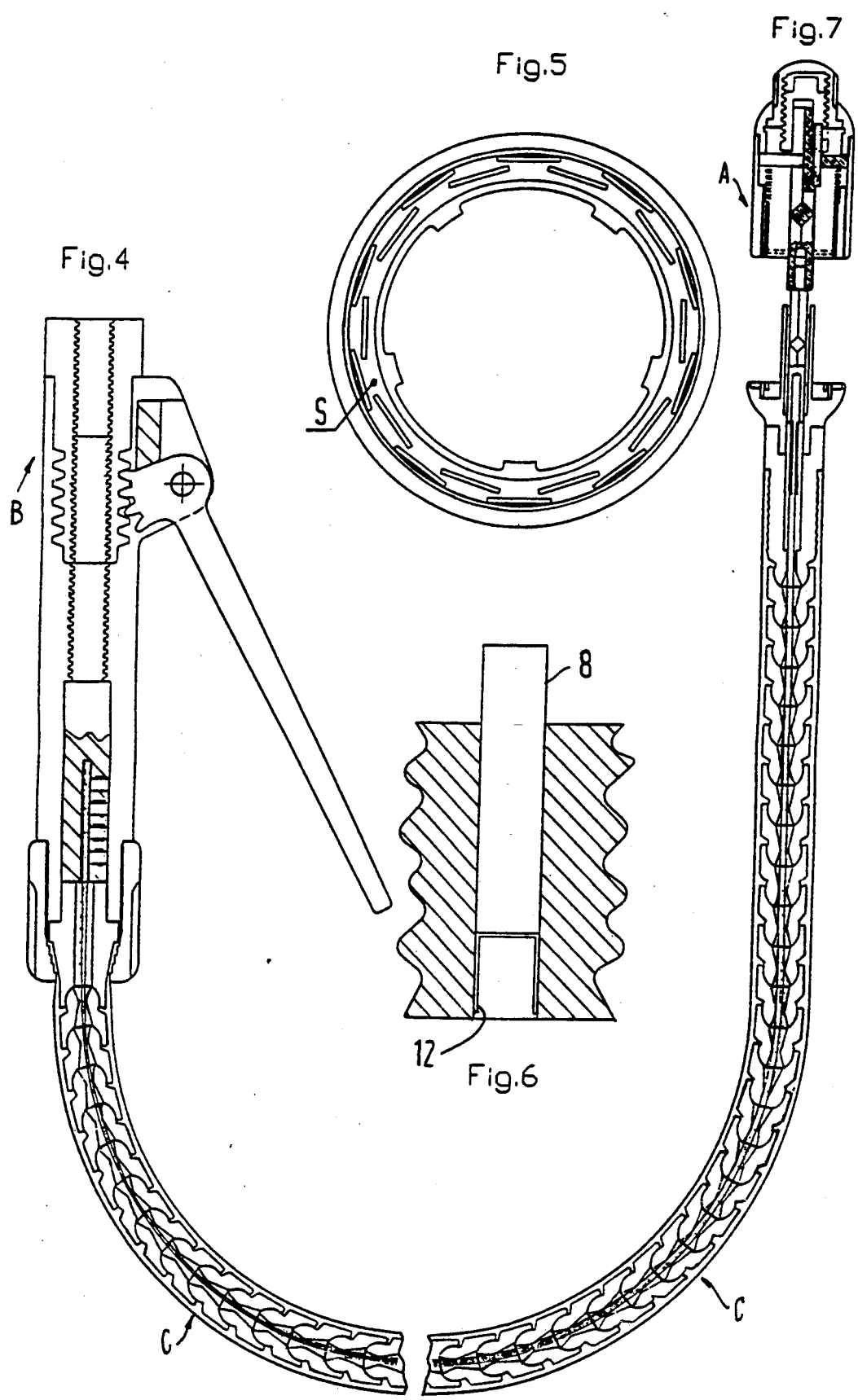

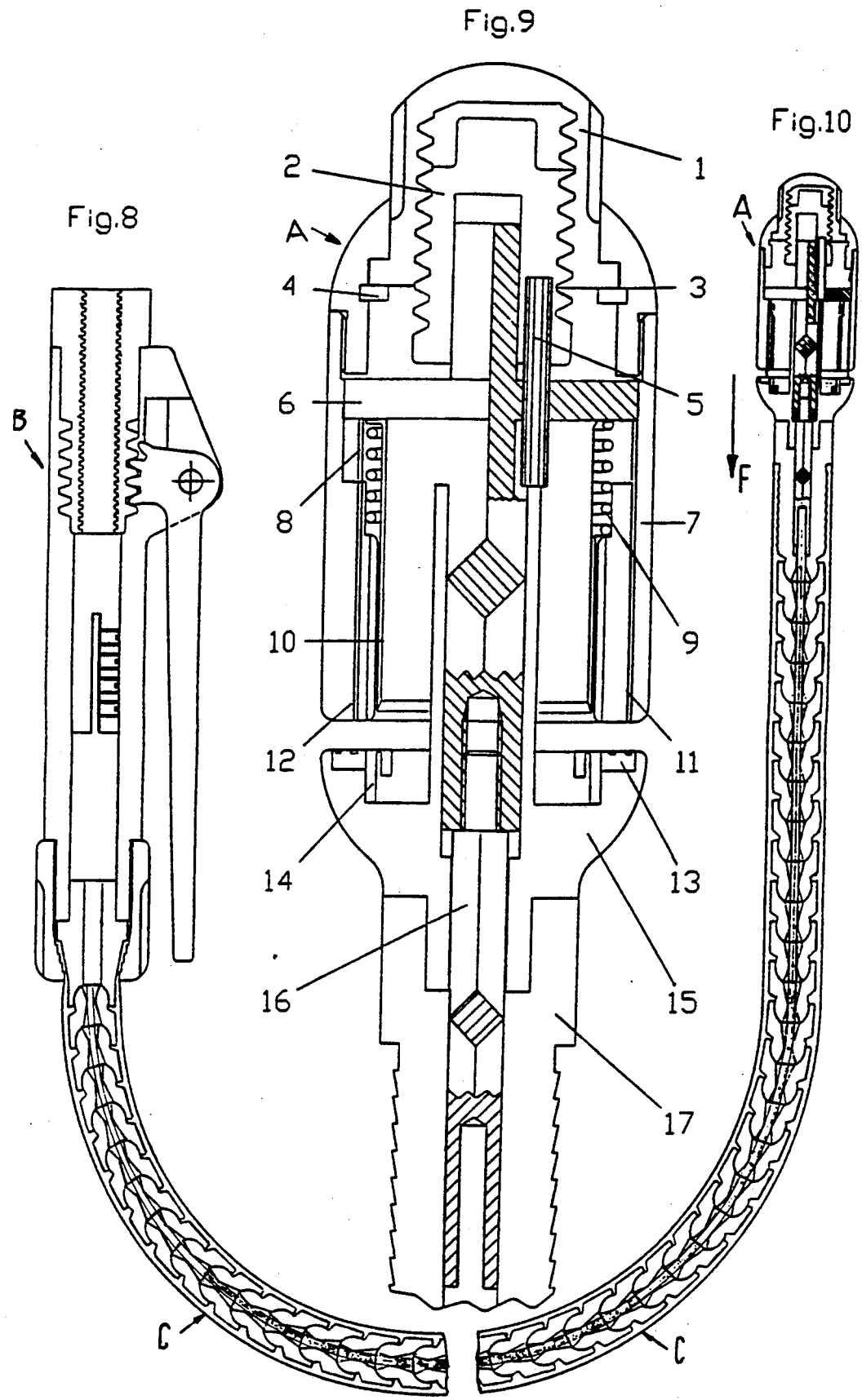

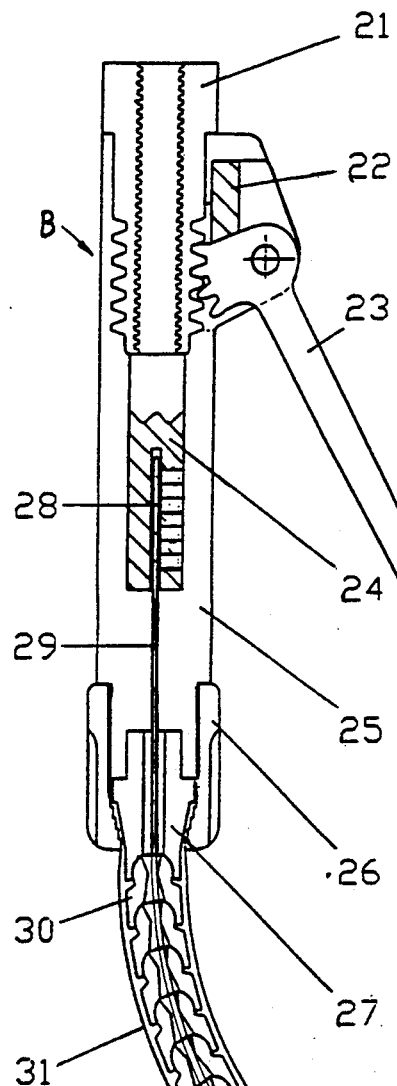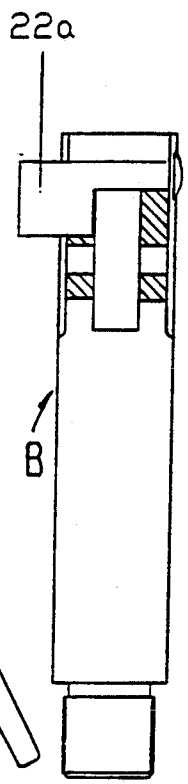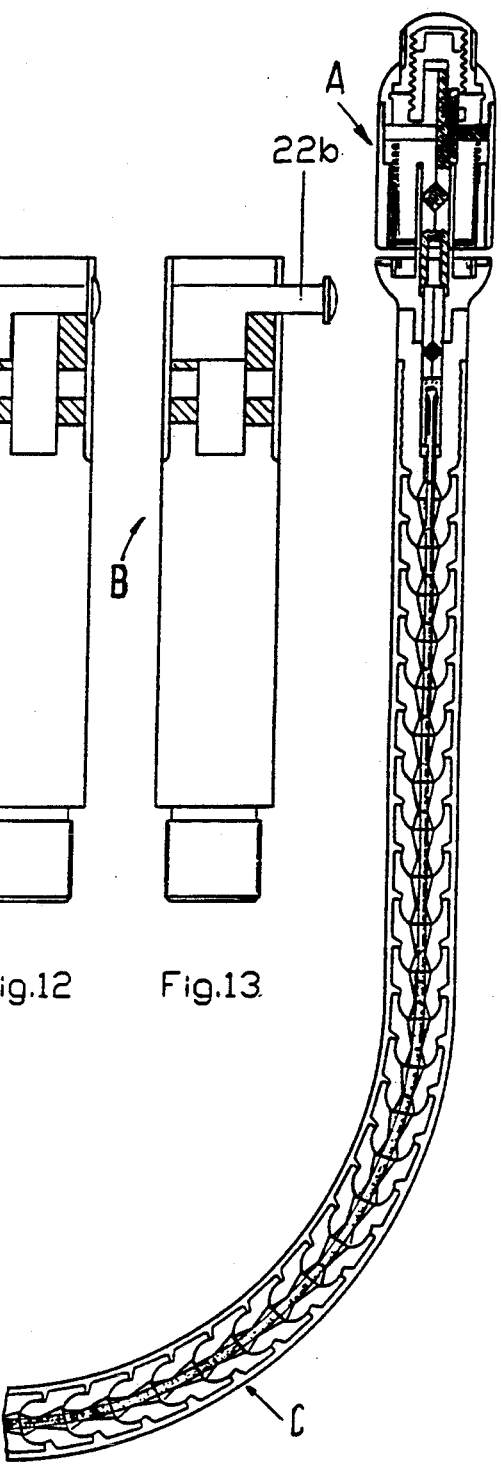
Fig.11  Fig.12  Fig.13  Fig.14

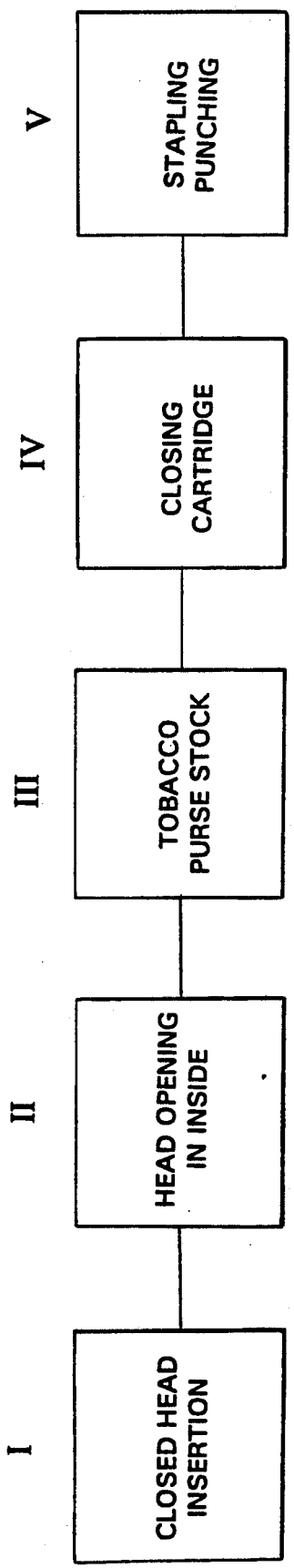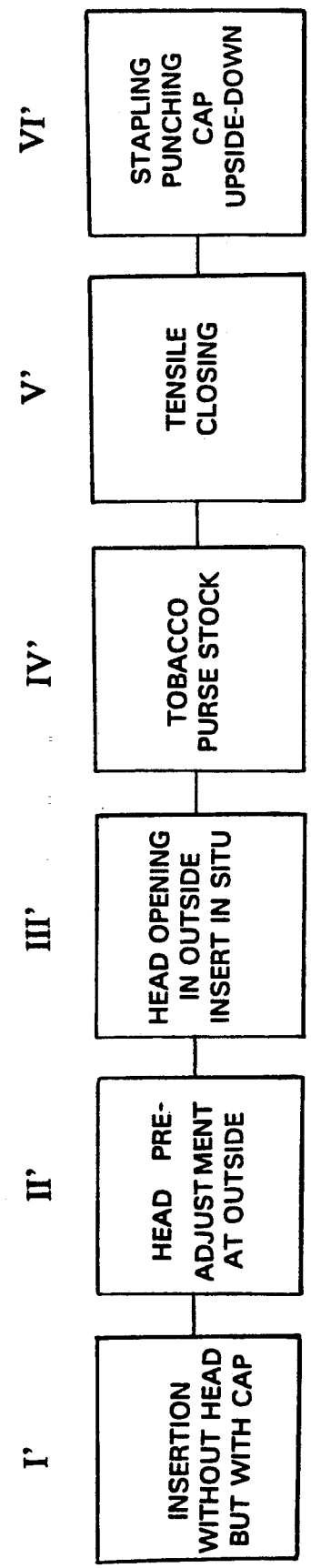

APPARATUS AND METHOD FOR SUTURING

BACKGROUND OF THE INVENTION

1. Field of the Invention

The present invention relates to an apparatus and related method for making surgical sutures and, in particular, sutures for connecting two open sections of a duct or tubular element of the human or animal body.

2. Description of the Related Art

As is well-known, a stapler for surgical operations is used for carrying out the mechanical connection, followed by the natural biological connection, of two open sections of ducts of the human or animal body. The two sections are previously prepared with the aid of equipment suitable for forming onto the ends of the sections a binding of the type known as a "purse bag". The stapler is introduced into one of the two sections through an opening that is accessible (e.g. in the intestine, through the rectum), until its end reaches the zone of operation where the separated sections are pressed by a cartridge fixed to the head of the stapler and are joined mechanically through staples supplied from the cartridge. The excess organic tissue part in the inside of the duct is removed by a punching operation performed by the same stapler after the stapling. Thereafter, by extracting the stapler out of the opening (e.g. the rectum), the excess tissue cut by the hollow punch is recovered. After a certain time, organic uniting of the two sections in the connection zone occurs, and the tissue mechanically joined through the staples is eliminated naturally by excretion.

Systems and equipment for carrying out this important surgical operation are widely described in the literature. For example, U.S. Pat. No. 4,485,817 describes a stapler including: a head for applying staples to the tissue, including a member for the application of the staples from a cartridge, and an anvil; means for controlling the elements of the head; and drive means between the head and the control means, including a flexible shaft that can be bent during insertion and can be adapted to the configuration of the opening of the human body and can hold the assumed configuration during the operation.

The equipment described in this patent reference has various advantages—in particular, that of providing a surgical stapler with a flexible shaft—but it also has many drawbacks, including the irremovability of the head, the necessity of adjusting it "in situ", its operation by compression and, above all, the necessity of having a large diameter of the articulated pipe to be introduced into the duct to be sutured. In all cases, this diameter cannot be reduced to make insertion easier. Further, the control is rather complex and its flexibility and memory are limited.

For the purpose of explanation, FIG. 18 shows the operative method of the conventional equipment, including the one according to U.S. Pat. No. 4,485,817. As shown in FIG. 18, phase I includes inserting the stapler with a closed head (with diameter e.g. of 32 mm); phase II comprises opening the head in the inside of the intestinal duct (turning the pushbutton of the control device); phase III comprises forming the tobacco purse; phase IV is the closing of the cartridge (turning the pushbutton in opposite direction); and phase V comprises the operation of stapling and hollow punching.

The whole operation is painful for the patient and also requires complicated efforts by the surgeon who must perform all these phases and motions manually.

SUMMARY OF THE INVENTION

An object of the present invention is to provide a surgical stapler that does not have the above-mentioned drawbacks—in particular, a stapler which is not provided with a head in the insertion phase and therefore has a small diameter and yet has the ability to allow preadjustment of the head externally.

Another object of the invention is to provide a method for the rapid execution of sutures with maximum operative safety, with minimal danger and without contamination, and further without the necessity of requiring the intervention of the surgeon in all phases.

The above and other objects of the invention are achieved by an apparatus for making surgical sutures comprising: a distal head member-comprising surgical staple supplying means adapted to receive surgical staples and further comprising an anvil against which the staples supplied from the staple supplying means are formed; a proximal control member having adjusting means disposed therein; flexible drive means having a proximal and a distal end coupling the distal head member and the proximal control member, the drive means transmitting control movements of the control member to the head member; the head member being removably detachable from the flexible drive means, the distal end of the flexible drive means being insertable into a tissue duct to be sutured through an opening in the duct when the head member is detached from the distal end of the flexible drive means, the head member being attachable to the distal end of the flexible drive means after the distal end has been inserted into the tissue duct, the distal end of the flexible drive means having a diameter smaller than the distal head member whereby the distal end of the flexible drive means may be easily inserted into an opening in a tissue duct.

The method according to the invention is characterized substantially in that the insertion of the stapler is made after having removed the head, the preadjustment of which is made externally, either by the surgeon or hospital personnel.

In summary, the main characteristics of the invention are the detachable head and the preadjustment thereof externally, and also the characteristics arising from the facts that: the head works in the contrary direction (with respect to the above-mentioned U.S patent)—that is, by drawing and not by compression; the control element is simple—that is, it includes a single tie rod or wire; the flexible pipe is a body that can be bent at least 90° and does not tend to straighten under any minimum stress; the apparatus operates with a cartridge upside down that is, the fixed part is used as anvil and the mobile part is used as hammer; the cartridge is mounted by the surgeon at the last moment in the stapling zone after the flexible part has made the path along the duct and has reached the sections in the zone to be stapled. This action allows the insertion, into the intestine or other pipe or duct, of a device having a smaller diameter (about half the diameter) that damages in a limited manner the opening and the pipe or duct. A safety system that signals to the surgeon, by a change of effort, that the punching of the intestine has occurred is also provided.

The apparatus according to the invention is also advantageous, as it can be sterilized completely mounted and in a single operation by ethylene oxide, instead of using the differentiated sterilizations for individual parts by steam and/or solutions according to well-known techniques.

The different characteristics and advantages of the invention will be apparent from the description which follows.

Other features and advantages of the present invention will become apparent from the following description of the invention which refers to the accompanying drawings.

BRIEF DESCRIPTION OF THE DRAWINGS

The invention will be described in greater detail in the following detailed description with reference to the drawings, in which:

FIGS. 1, 4, 8, 11 and 15 show the control device B (at the left end in each of the figures) of the stapler according to the invention in the following positions:

FIG. 1 shows the rest position;

FIG. 4 shows the control device adjusted so the cartridge (FIG. 7) is in its open position for arranging the two sections of organic tissue to be sutured;

FIG. 8 shows the control device of the stapler after stapling and punching have just been made;

FIG. 11 shows the control device of the stapler when the cartridge has been preadjusted externally, e.g. by the surgeon or by his assistant, using a pawl of the invention, according to the thickness of the tissue to be sutured; and FIG. 15 shows the control device of the stapler during the reopening phase.

FIGS. 3, 7, 9, 10, 14, 16 and 17 show partial sectional views of the operative part and the anvil (part A), comprising the stapler head in the corresponding positions specified above for the control device, in particular:

FIG. 3 shows the end of the stapler with suturing cartridge mounted (see also FIG. 9);

FIG. 7 shows the cartridge in a position of use;

FIG. 9 shows the components of the preadjusted cartridge, in enlarged scale;

FIG. 10 shows the cartridge after stapling and punching (see FIG. 8);

FIG. 14 shows the preadjusted cartridge, as in FIG. 10;

FIG. 16 shows the cartridge after punching with yielding of a safety ring 14 to be described (see also FIG. 9);

FIG. 17 shows the cartridge during the reopening phase;

FIG. 2 shows the details of the stapler end without the head, but provided with a cap 32 that is used in the introduction phase to make insertion through an organic opening easy;

FIG. 5 is a bottom view of the layout of the seats S of the staples (shown at 11 and 12 in FIG. 9);

FIG. 6 is a lateral sectional view of the cartridge with a view of the staple in its seat S and tongue (shown at 8 in FIG. 9) that pushes the staple;

FIGS. 12 and 13 show the safety system 22 (see FIG. 11) when inserted (22a) and disengaged (22b), respectively; and FIGS. 18 and 19 are two block diagrams showing the conventional method and the method according to the present invention, respectively.

DETAILED DESCRIPTION OF THE DRAWINGS

Figure 15:
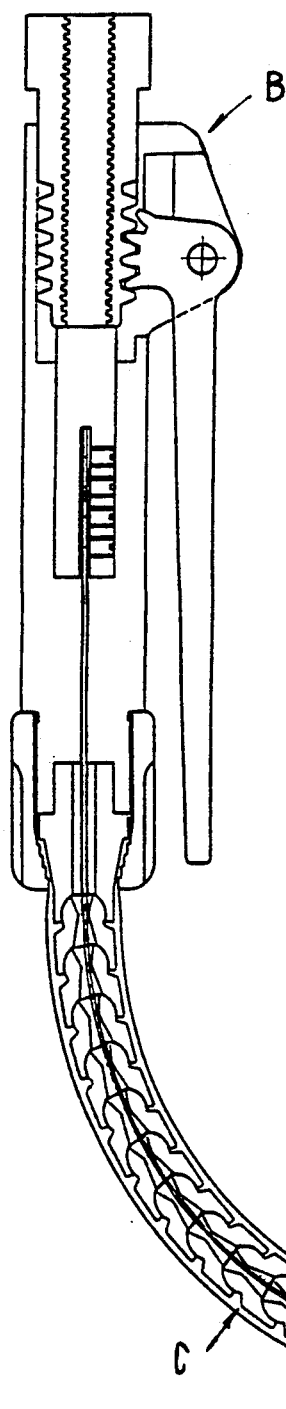

With reference now to the drawings, the apparatus according to the invention includes at the left end a device B including components 21, 22 and 23 controlling the stapler, an intermediate drive means C including flexible member 31 and a means A for application of the staples at the other end, shown at the right in the drawings. Starting with means A shown in FIGS. 3, 7, 10, 14, and 17 in a reduced scale, but at the center of the drawing sheets of FIGS. 9 and 16 with enlarged scale, the staple applicator includes a graduated pushbutton or pawl 1 (FIG. 9) for the preadjustment of the head according to thickness of the organic tissue to be stapled; a threaded cursor 2 for establishing the minimum closing distance of the cartridge, whose main body is indicated by 7 and whose internal sheath is indicated by 3; a ring 4 preferably made of stainless steel for holding the pawl 1; a pushing cylinder 5 between the base 15 and the cursor 2; and a mobile plane 6 for the moving tongue 8, which in turn controls staples 11 and 12 and a hollow punch 10.

The cartridge includes the main body 7, spring 9 for holding the hollow punch 10 and the cursor 2 in position, and the tongues 8 for controlling the external stapler 11 and the internal staples 12 (See FIG. 5).

Under the lower base of the head is located an anvil or ring 13 for riveting the staples 11 and 12, a safety ring 14 and a connection base 15 to the flexible part C.

Figure 16:
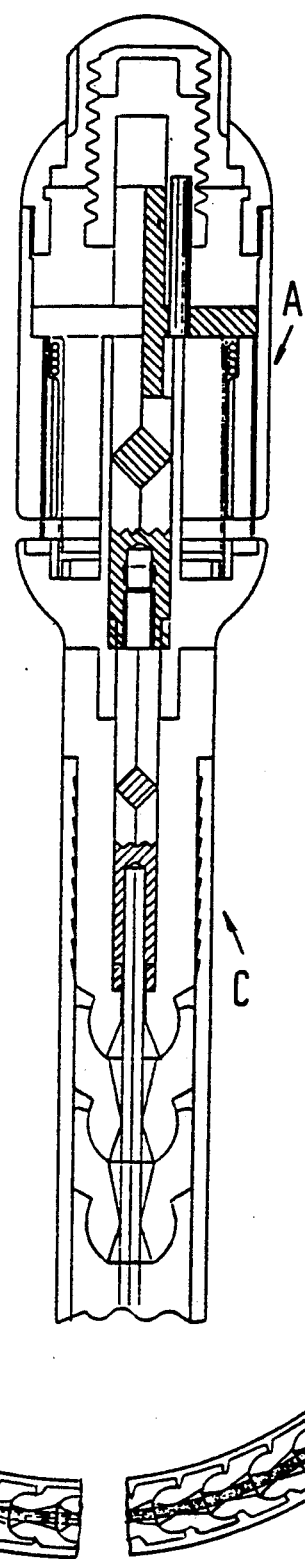
Figure 17:
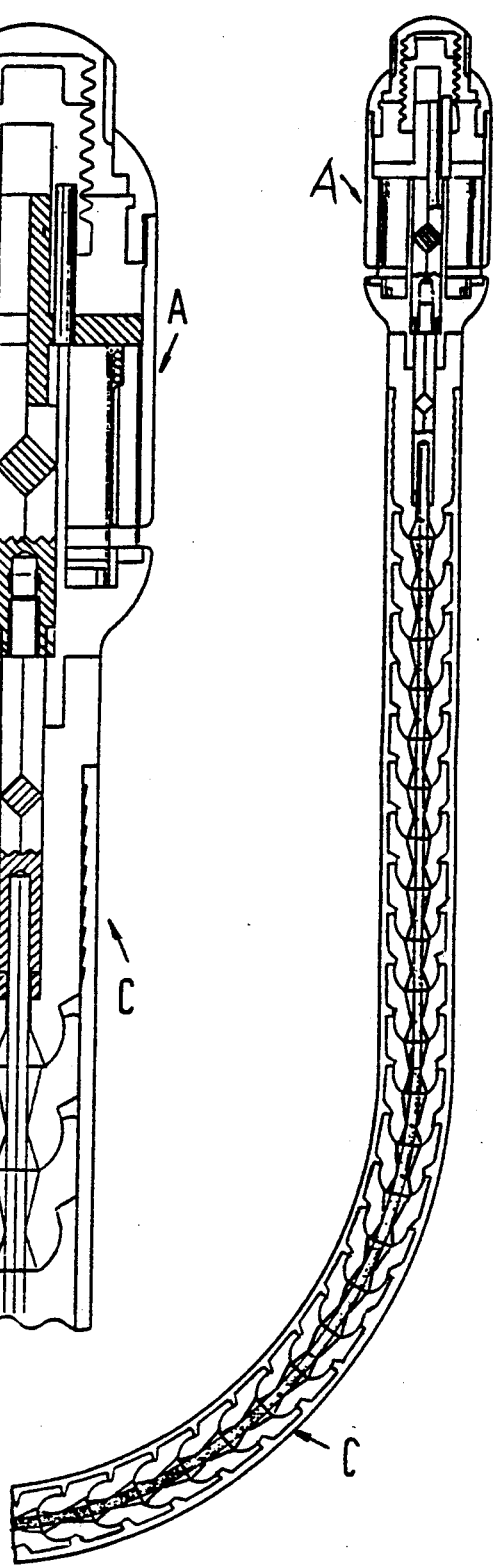

The flexible transmission means C between the control device B, to be described in the following, and the anvil head A is represented in greater detail and with enlarged scale in FIGS. 2 and 16. It includes an external sheath 31, a closing cap 32, a tie rod 18 having a shaped end 16, a body 17 for receiving the cartridge and articulated junctions 19.

FIG. 2 shows the interface between the transmission means C and part A, that is the head A, including main body 7 and anvil 13. FIGS. 1 and 11 show, in detail, the control device B, including a toothed lever 23 engaging a rack, the rack being in engagement with the external teeth of a knob 21 for adjustment of the opening of the cartridge 7. (FIG. 3 shows the end of the stapler with staple cartridge A mounted and FIG. 7 shows the cartridge in a position of use.)

Turning to FIG. 1, reference numeral 24 shows the lower end of a tie rod 29 (which is an extension of the tie rod 18), while reference numeral 28 shows a mechanical device for coupling the tie rod 29 and a member 24

The lower part of the control device showing the insertion of the flexible cable into the control device B includes a ring nut 26 for locking the sheath 31 and a corresponding end 27 of a hinge connection to the control device main body 25, the hinge connection denoted by 30. The control device B includes also a safety element 22 that, in FIG. 12, assumes the position 22a when engaged, while FIG. 13 shows position 22b when it is released. FIG. 5 shows a bottom view of the layout of the seats S of the staples (corresponding to details 11 and 12 of FIG. 9), while FIG. 6 shows a lateral section of the cartridge with a view of a staple 12 into its seat S and the tongue 8 (see FIG. 9) that pushes the staple.

The apparatus according to the invention operates as follows:

Depending on the thickness of the intestine or tissue duct of the person or animal to be operated upon, the operator adjusts the initial distance between the anvil 13 and the main body 7 by moving the graduated pushbutton 1. Advantageously, the adjustment is made out of the zone of the operation, even if it is made in situ. The operating part of the apparatus is introduced (as represented, through the opening available in the human body, e.g. the rectum opening for the intestine in FIG. 9) without the cartridge, but with protective cap 32 mounted. After having prepared the part to be stapled, e.g. the intestine, the protective cap 32 is removed and the head A is screwed on. Using the knob 21 located on the lever handle 23, the main body 7 is moved away from anvil 13, e.g. to a 25 mm distance, for making insertion easier into the intestine and the related bag closing. Moving the knob 21 located on the lever handle, the main body 7 is moved toward the anvil 13 in the direction of the arrow F (see FIG. 9). The intestine cannot be flattened more than the space left free during the preadjusting phase. When it arrives at its stop, the knob 21 encounters a high resistance. By then operating the lever 23, the plane 6 is moved against the spring 9. The tongues 8 urge the staples 11 and 12 toward the anvil 13, closing them. Contemporaneously, the hollow punch 10 cuts the intestine and breaks the safety ring 14, signaling that the operation is over.

A first feature of the invention is related to the fact that the head can now be removed and initially, that is, at the insertion, the head is removed and adjusted from the outside According to a second feature of the invention, the head is driven by pulling it in the direction of the arrow F. Initially, the knob 21 is turned in a clockwise direction, and the knob 21 acting on the cable 18 pulls it and therefore the body 7 is moved until the cylinder 5 forming a limit stop engages the lower body 15 comprising related thrust bearings. At this moment, the operator feels a resistance to any further progress of the head in the direction F, this resistance being caused by the spring 9 that presses against the hollow punch 10.

As above mentioned, at this moment, the rotation of the knob 21 is stopped, the knob 21 is released and the rack lever 23 is operated, which continues the traverse of the hollow punch 10 with multiplied force; the same lever 23 pushes contemporaneously the staples 11 and 12 until they are brought against the anvil 13. In this manner, it starts the bending of the staples 11 and 12 that have just crossed the two edges of the tissue and, continuing the stroke, the punch end 10 cuts the intestinal tissue and the ring 14, alerting the surgical operator that the operation is over and that the staples 11 and 12 are now closed around the edges of the tissue. This cutting position is signaled acoustically by a sound "tac", indicating the yielding of the ring 14 and mechanical engagement of the limit stop.

According to another feature of the invention, a flexible pipe, including a series of pressed and embedded spherical hinges 30 (preferably made of polyamide plastics), is used. The ring nut 26 locks the sheath 31. The end of the spherical hinge is shown at 27. It is essential that the play between the tie rod 28 and the zone of lesser diameter be reduced to a minimum value. The flexible pipe can be covered by a sheath 31. For operating lever 23 at the end of the rotation of the knob 21, the lever must be unlocked by operating a safety wedge 22, which releases the lever. The positions of the safety device 22 are indicated by 22a and 22b in FIGS. 12 and 13.

With reference now to the block diagram shown in FIG. 19, phase I' shows that the apparatus is inserted without head A, but with protecting cap 32. Therefore, the diameter is practically the diameter of the flexible pipe and can also be less than 15 mm. In phase II', the preadjustment of the head is made externally, while in phases III', IV', V' and VI', the phases of opening the head preparing the tobacco purse sock, cartridge closing and stapling and hollow punching are performed.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

I claim:

1. A method of suturing a tissue duct with a stapling apparatus, the stapling apparatus including:
    a distal head member comprising a staple supplying means adapted to receive surgical staples and further comprising an anvil against which said staples supplied from said staple supplying means are formed;
    a proximal control member having adjusting means disposed therein;
    drive means having a proximal and a distal end coupling said proximal control member and said distal head member, respectively said drive means transmitting control movements of said control member to said head member;
    said head member being removably detachable from said drive means, said distal end of said drive means being insertable into a tissue duct to be sutured through an opening in said duct when said head member is detached from said distal end of said drive means, said head member being attachable to said distal end of said drive means after said distal end has been inserted into said tissue duct, said distal end of said drive means having a diameter smaller than said distal head member whereby said distal end of said drive means may be easily inserted into an opening in a tissue duct;
    the method comprising inserting the distal end of the flexible drive means into an opening in the tissue duct, inserting the head member into the duct through another opening near a zone in which suturing is to take place, attaching the head member to the distal end at the zone in which suturing is to take place, and operating the control member of the stapling apparatus to make a suture.

2. The method recited in claim 1, further comprising the step of providing a removable protective cap on said distal end prior to insertion into the tissue duct and further comprising removing the cap after said distal end reaches the zone in which suturing is to take place prior to attachment of said head member.

3. The method recited in claim 1, further comprising preadjusting a spacing between the anvil and said staple supplying means depending on the thickness of a tissue to be sutured externally of said zone in which suturing is to take place and prior to attachment of said head member to said distal end of said drive means.

4. The method recited in claim 1, wherein said head member comprises two separated sections, one section comprising said staple supplying means and the other section comprising said anvil, said method further comprising attaching said anvil to said distal end of said drive means first in the zone in which suturing is to take place and subsequently attaching said staple supplying means to said distal end, with a prescribed space between said staple supplying means and said anvil adapted to receive a tissue to be sutured therebetween.

5. The method recited in claim 1, further comprising the step of adjusting a spacing between the anvil and said staple supplying means depending on the thickness of a tissue to be sutured in situ in the zone where suturing is to take place.

6. The method recited in claim 5, wherein said stapling apparatus comprises a control element for adjusting the spacing between said staple supplying means and said anvil, said control element disposed at said proximal control member, the method further comprising moving said control element to adjust said spacing in situ in the zone where suturing is to take place.

7. The method recited in claim 1, wherein said drive means is flexible, further comprising bending said drive means into a convenient shape for use.

8. A method of using a surgical stapler to suture a tissue duct comprising the steps of:
   inserting an end of a drive member of said stapler into an opening in the tissue duct, the drive member having a diameter consistent with the opening size;
   moving the end of the drive member toward a zone in which suturing is to take place;
   inserting a head member containing surgical staples into the tissue duct, the head member to be attached to the end of the drive member in the zone in which suturing is to take place;
   connecting the head member to the end of the drive member; and
   controlling the head member through the drive member to form a surgical suture with a control member of the stapler connected to an opposite end of the drive member.

9. The method recited in claim 8, further comprising the step of separating the head member into two components, the two components comprising a stapling cartridge containing staples and an anvil, and attaching the anvil first to the end of the drive member and subsequently attaching the cartridge to the anvil.

10. The method recited in claim 9, wherein said step of separating is performed in the zone in which suturing is to take place.

11. The method recited in claim 8, wherein the head member comprises two components, said two components comprising a stapling cartridge containing staples and an anvil, and further comprising the step of adjusting a spacing between the anvil and the cartridge.

12. The method recited in claim 11, wherein the step of adjusting the spacing is made prior to the step of inserting said head member into the tissue duct.

13. The method recited in claim 11, wherein the step of adjusting the spacing is made after the step of inserting said head member into the tissue duct.

14. The method recited in claim 13, wherein the step of adjusting the spacing is made after the step of connecting the head member to the end of the drive member.

15. The method recited in claim 8, further comprising the step of removing the head member from the end of the drive member, and placing a protective cap on said end of the drive member prior to said step of inserting the end of the drive member into the opening in the tissue duct.

16. The method recited in claim 15, further comprising removing the protective cap once the end of the drive member is inserted into the tissue duct at the zone in which suturing is to take place prior to connecting the head member to the end of the drive member.

17. The method recited in claim 16, further comprising discarding the protective cap.

18. Apparatus for making surgical sutures, comprising:
   a distal head member comprising surgical staple supplying means adapted to receive surgical staples and further comprising an anvil against which said staples supplied from said staple supplying means are formed;
   a proximal control member having adjusting means disposed therein;
   flexible drive means having a proximal and a distal end coupling said proximal control member and said distal head member, respectively, said drive means transmitting control movements of said control member to said head member;
   said head member being removably detachable from said drive means, said distal end of said drive means being insertable into a tissue duct to be sutured through an opening in said duct when said head member is detached from said distal end of said drive means, said head member being attachable to said distal end of said drive means after said distal end has been inserted into said tissue duct, said distal end of said drive means having a diameter smaller than said distal head member whereby said distal end of said drive means may be easily inserted into an opening in a tissue duct;
   said flexible drive means comprising a cable in a sheath, said proximal control member comprising means for moving said cable member in said sheath to effectuate relative movement of said staple supplying means and said anvil of said distal head member, said sheath of said distal end of said flexible drive means being detachably coupled to said anvil, adistal member in said sheath to effectuate relative movement of said staple supplying means and said anvil of said distal head member, said sheath of said distal end of said flexible drive means being detachably coupled to said anvil, a distal end of said cable detachably coupled to said staple supplying means, said control member moving said staple supplying means and anvil relatively together by transmission of a control movement through said cable of said flexible drive means such that said cable moves said staple supplying means toward said anvil to form said surgical staple and make a suture.

19. The apparatus recited in claim 8, further comprising a removable cap attachable to said distal end of said drive means for protecting said distal end of said drive means when said distal end is inserted into the tissue duct.

20. The apparatus recited in claim 19, wherein said removable cap is disposable.

21. The apparatus recited in claim 7, wherein said distal head member further comprises cutting means for cutting excess tissue during a suturing operation.

22. The apparatus recited in claim 21, wherein said cutting means comprises a cylindrical scalpel for cutting excess tissue in a tissue duct.

23. The apparatus recited in claim 21, wherein said anvil comprises a safety ring that provides a signal to a user that said cutting means has penetrated said excess tissue.

24. The apparatus recited in claim 23, wherein said safety ring provides a tactile signal to the user through said flexible drive means, said signal comprising a change of stress felt in said control member.

25. The apparatus recited in claim 23, wherein said safety ring is cut by said cutting means to provide an audible signal.

26. The apparatus recited in claim 18, wherein said staple supplying means and said anvil are detachable from each other, whereby said anvil can first be attached to said distal end of said flexible drive means in the tissue duct and said staple supplying means can secondly be attached to said distal end of said flexible drive means in the tissue duct.

27. The apparatus recited in claim 26, further comprising a space disposed between said staple supplying means and said anvil, said space being adjustable in accordance with the thickness of tissue to be sutured.

28. The apparatus recited in claim 18, wherein said sheath further comprises a plurality of articulated joints serially coupled together, said cable moving in said plurality of joints.

29. The apparatus recited in claim 28, wherein said articulated joints allow said flexible drive means to flex through at least 90°.

30. The apparatus recited in claim 29, wherein said flexible drive means retain a flexed position once such flexed position is attained until a stress is applied to change said position.

31. The apparatus recited in claim 29, wherein said articulated joints comprise a plastic material.

32. The apparatus claimed in claim 31, wherein said plastic material comprises a polyamide plastic.

33. The apparatus recited in claim 28, further comprising an external sheath member covering said articulated joints.

* * * * *